(12) United States Patent
Strother et al.

(10) Patent No.: US 9,211,202 B2
(45) Date of Patent: Dec. 15, 2015

(54) APPARATUS AND METHOD FOR TREATING AN ANEURYSM

(75) Inventors: Charles M. Strother, Madison, WI (US); Jingfeng Jiang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1846 days.

(21) Appl. No.: 12/258,264

(22) Filed: Oct. 24, 2008

(65) Prior Publication Data

US 2010/0106180 A1    Apr. 29, 2010

(51) Int. Cl.
*A61F 2/06* (2013.01)
*A61F 2/82* (2013.01)

(52) U.S. Cl.
CPC ............. *A61F 2/82* (2013.01); *A61F 2002/068* (2013.01); *A61F 2002/823* (2013.01)

(58) Field of Classification Search
CPC   A61F 2/82; A61F 2002/823; A61F 2002/068
USPC .................................. 606/200; 623/1.15–1.54
See application file for complete search history.

(56) References Cited

U.S. PATENT DOCUMENTS

| | | | | |
|---|---|---|---|---|
| 5,782,905 | A * | 7/1998 | Richter | 623/1.1 |
| 6,395,014 | B1 * | 5/2002 | Macoviak et al. | 606/200 |
| 6,409,697 | B2 * | 6/2002 | Eno et al. | 604/9 |
| 6,419,686 | B1 * | 7/2002 | McLeod et al. | 606/200 |
| 7,153,324 | B2 * | 12/2006 | Case et al. | 623/1.24 |
| 2003/0097172 | A1 * | 5/2003 | Shalev et al. | 623/1.31 |
| 2004/0260382 | A1 * | 12/2004 | Fogarty et al. | 623/1.11 |
| 2006/0206200 | A1 | 9/2006 | Garcia et al. | |
| 2008/0262604 | A1 * | 10/2008 | Stengel | 623/1.31 |

\* cited by examiner

*Primary Examiner* — Melanie Tyson
*Assistant Examiner* — Amy R Weisberg
(74) *Attorney, Agent, or Firm* — Armstrong Teasdale LLP

(57) ABSTRACT

In an apparatus and method for treating an aneurysm, a flow control member is positioned within a blood vessel at least in part upstream of an aneurysm and extending radially inward of the blood vessel wall into the flow path of blood flowing within the blood vessel. The flow control member alters the blood flow path within the blood vessel upstream of the aneurysm to inhibit blood flow to the aneurysm. A retention member may be positioned within the blood vessel at least in part upstream from the aneurysm and having an outer surface engageable with the blood vessel wall. In such an instance, the flow control member is retained by the retention member and extends radially inward of the blood vessel wall upstream from the aneurysm.

11 Claims, 12 Drawing Sheets

US 9,211,202 B2

APPARATUS AND METHOD FOR TREATING AN ANEURYSM

CROSS REFERENCE TO RELATED APPLICATIONS

The present disclosure is directed to the treatment of aneurysms, and more particularly to apparatus and methods for altering the blood flow path within a blood vessel to inhibit blood flow to the aneurysm.

Aneurysms, which are localized, blood-filled dilations (e.g., balloon-like bulges) of a blood vessel caused by disease or weakening of the vessel wall, are a common and frequently lethal disease. Aneurysms are most often found in the brain (commonly referred to as intracranial, or cerebral aneurysms) and the aorta, although other areas such as the legs, intestine and spleen are also know locations of aneurysms. Intracranial aneurysms, as an example, are estimated to be prevalent among one to six percent of the adult population in the United States. Of these several million people, an estimated 30,000 will suffer rupture, of which 50 percent will die and another 20-30 percent will suffer severe neurological injury.

Aneurysms typically result from a combination of interactions between physical, genetic and environmental factors. Key physical factors of intracranial aneurysm development, for example, include the anatomy of of intracranial arteries (e.g., thin walls with only a single elastic lamina) and hemodynamic forces (e.g., shear stress and gradient, flow impingement and particul/molecular residence times). The strategy for treating intracranial aneurysms has generally been to prevent rupture by isolation of an aneurysm from the circulation either by using an open surgical technique to place a clip across its base, or neck, or more recently by using an endovascular technique.

Over the last decade, endovascular techniques have become the treatment of choice for a majority of intracranial aneurysms. These techniques, often referred to as coil embolization, or coiling, typically involve direct catheterization of an aneurysm and then positioning and deployment of a series of detachable metallic coils within the aneurysm cavity. In particular, a catheter is inserted into the femoral artery in the patient's leg and navigated through the vascular system into the head, and into the aneurysm. Tiny platinum coils (so that they are visible by X-ray) are deployed into the aneurysm to block further blood flow to the aneurysm and thereby prevent rupture.

This technique has been shown to be effective in treating intracranial aneurysms. There is, however, still significant morbidity and some mortality associated with coiling as well as with the traditional open surgical clipping. There is also an even more significant incidence of aneurysm recurrences after what had seemed, immediately post-treatment, to be successful coiling. This is particularly so in those aneurysms larger than 10 mm in their greatest diameter. Because of this uncertainty about durability, patients are required to undergo follow-up procedures at regular (e.g., six months, or one year) intervals for at least 3-5 years. Moreover, this technique does not address in any way the abnormal physiology (e.g., hemodynamics) that are thought to be responsible for intracranial aneurysm origin, growth and rupture.

There is a need, therefore, for an aneurysm treatment apparatus and method that can eliminate or relieve abnormal hemodynamics at or near the site of an aneurysm and/or provide isolation of an aneurysm from the blood circulation in such a way that recurrences may be reduced or eliminated.

In one aspect, apparatus for treating an aneurysm generally comprises a retention member positionable within a blood vessel at least in part upstream from an aneurysm and having an outer surface engageable with the blood vessel wall, a flow control member is retained by the retention member and extends radially inward of the blood vessel wall upstream from the aneurysm to alter the flow of blood flowing within the blood vessel prior to the blood flowing past the aneurysm.

In one aspect of a method for treating an aneurysm, a flow control member is positioned within a blood vessel at least in part upstream of an aneurysm and extending radially inward of the blood vessel wall into the flow path of blood flowing within the blood vessel. The flow control member alters the blood flow within the blood vessel upstream of the aneurysm to inhibit blood flow into the aneurysm.

In another aspect of a method for treating an aneurysm, the method relates to treating an aneurysm of a blood vessel configuration that includes a parent blood vessel, a first branch blood vessel and at least a second branch blood vessel both branching from the parent blood vessel, the aneurysm being located generally at the point at which the parent blood vessel branches into the first and second branch blood vessels. The method generally comprises positioning a retention member at least in part within the parent blood vessel. The retention member is tubular and has a side wall constructed such that the side wall is permeable to blood flowing within the parent blood vessel. The position of the retention member is such that blood flowing through the parent blood vessel flows through the side wall of the retention member into at least one of the first and second branch blood vessels. A flow control member is deployed in the retention member to alter the flow of blood through the retention member and away from the aneurysm without occluding the aneurysm itself.

Other features of the invention will be in part apparent and in part pointed out hereinafter.

BRIEF DESCRIPTION OF DRAWINGS

Corresponding reference characters indicate corresponding parts throughout the several views of the drawings.

DETAILED DESCRIPTION OF THE EXEMPLARY EMBODIMENTS

Figure 1:
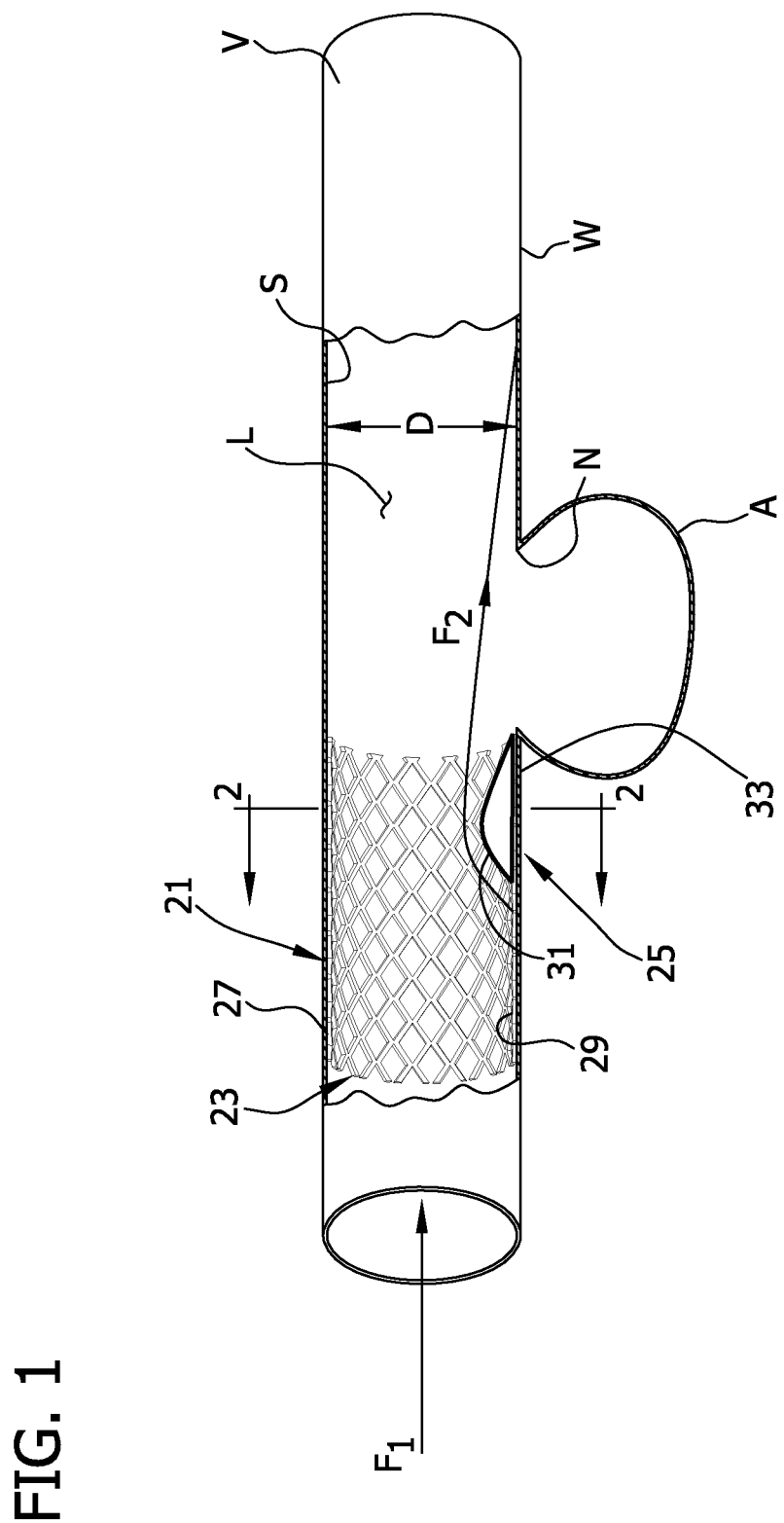
FIG. 1 is a schematic illustration of a blood vessel having an aneurysm and one embodiment of an apparatus for treating an aneurysm, with portions of the blood vessel and a retention member of the apparatus cut away to reveal internal configuration and with flow arrows indicating blood flow direction.
Figure 2:
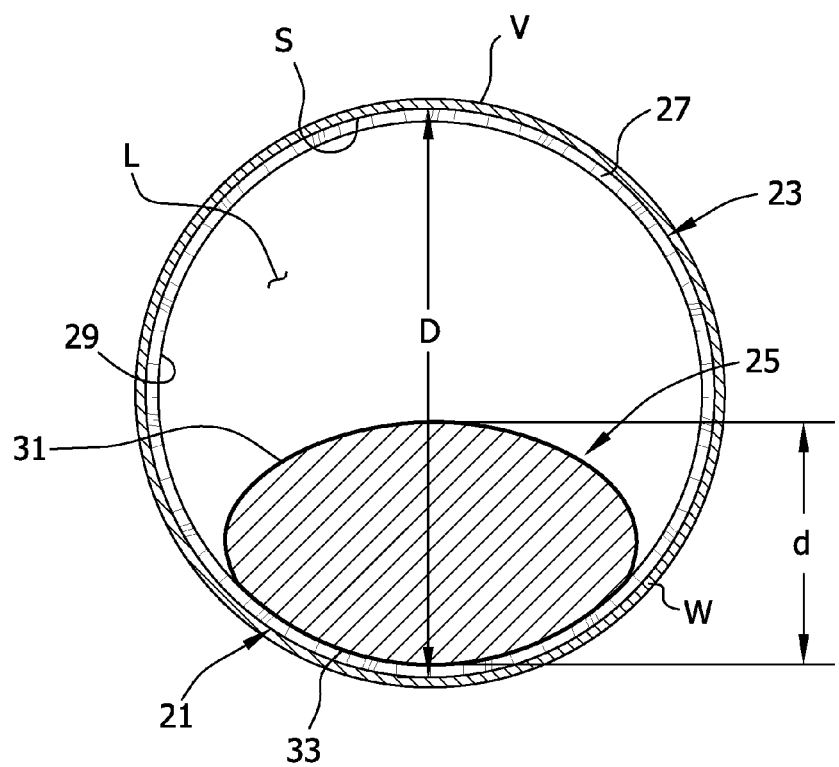
FIG. 2 is a cross-section taken in the plane of line 2-2 of FIG. 1.

With reference now to the drawings and in particular to FIGS. 1 and 2, a blood vessel V (such as, for example, an intracranial artery) has a vessel wall W having a luminal surface S defining an inner diameter D of the vessel wall and an interior lumen L along which blood flows through the vessel such as in the direction indicated by flow arrow F1 in FIG. 1. The illustrated blood vessel V has an aneurysm A including a neck N open to the lumen. Apparatus according to one embodiment for treating an aneurysm is generally indicated at 21 and comprises a retention member, indicated generally at 23 for locating and maintaining the position of the apparatus in the blood vessel V, and a flow control member, indicated generally at 25, for altering the flow of blood past the aneurysm A. In particular, the apparatus 21 of this embodiment is configured to alter the flow of blood past the aneurysm A without occluding or sealing the aneurysm and without packing the aneurysm with coils, balloons or other known packing elements.

The retention member 23 illustrated in FIGS. 1 and 2 is suitably tubular, having an outer surface 27 engageable with the luminal surface S of the blood vessel wall W to generally retain the retention member at a predetermined location within the blood vessel V. An inner surface 29 of the retention member 23 faces inward away from the luminal surface S of the blood vessel wall W. In one particularly suitable embodiment, the retention member 23 is sized and constructed for delivery and deployment into the blood vessel V at a predetermined location relative to the aneurysm A by conventional techniques such as using a catheter or microcatheter and guide wires. It is understood, however, that the retention member 23 may be delivered to and deployed in the blood vessel V by other suitable techniques without departing from the scope of this invention.

More suitably, the retention member 23 is constructed of a material that can be folded, compacted and/or constrained in a catheter for delivery to the predetermined location in the blood vessel V and then expanded upon deployment, e.g., against the luminal surface S of the blood vessel wall W, to retain the retention member against further movement relative to the blood vessel V. A radial strength, or radially outward bias of the retention member 23 may suitably be only sufficient to stabilize the apparatus 21 in the blood vessel V (e.g., as opposed to substantially expanding the blood vessel). However, it is understood that the radial strength or bias of the retention member 23 may expand the blood vessel without departing from the scope of this invention.

As one example, the retention member 23 may be constructed of a shape memory alloy (SMA), which is known in the art as being capable of plastic deformation and returning to its pre-deformed shape upon exposure to thermal activation. For example, the retention member 23 may be constructed of nickel titanium (NiTi), also commonly referred to by its trade name Nitinol. Above its transformation temperature, Nitinol is superelastic, able to withstand a small amount of deformation when a load is applied and return to its original shape when the load is removed. Below its transformation temperature, it displays the shape memory effect. When it is deformed it will remain in that shape until heated above its transformation temperature, at which time it will return to its original shape. It is understood, however, that the retention member 23 may be constructed of stainless steel or other suitable material, or combinations thereof, and remain within the scope of this invention.

The illustrated retention member 23 is suitably of a generally cage-like or open cell construction, such as in the manner of a stent, and is generally circular in cross-section (FIG. 2) along its length to engage the luminal surface S of the vessel wall W about the entire inner circumference of the vessel wall. It is understood, however, that the retention member 23 may still be tubular but shaped in cross-section other than circular, such as triangular, rectangular, elliptical, or other suitable shape. It is also understood that the retention member 23 may be non-uniform in cross-section along its length so as to be other than cylindrical, such as generally conical or frusto-conical, spherical, or other suitable shape. It is further contemplated that in other embodiments the retention member 23 may extend less than about the full inner circumference of the luminal surface S of the blood vessel wall W (e.g., having a generally semi-circular cross-section) and remain with the scope of this invention.

With particular reference to FIG. 1, the retention member 23 is suitably deployed in the blood vessel V so that at least a portion (i.e., a longitudinal extent) of the retention member is disposed upstream from the aneurysm A (i.e., upstream from the open neck N of the aneurysm) relative to the direction of blood flow F1 through the blood vessel. In such an embodiment, the cage-like or open cell construction of the retention member 23 allows the neck N of the aneurysm A to remain substantially unoccluded by the retention member. In a particularly suitable embodiment, as illustrated in FIG. 1, the retention member 23 is deployed entirely upstream from the aneurysm A so that no portion of the retention member covers the neck N of the aneurysm. It is understood, though, that the relative location of the retention member 23 upstream of the aneurysm is dependent on a predetermined target location of the flow control member 25 relative to the aneurysm.

The flow control member 25 is suitably constructed to be substantially impermeable to blood so that blood flowing within the blood vessel lumen L must flow around the flow control member. For example, the flow control member 25 may be constructed entirely from a material that is impermeable to blood. In other embodiments, the flow control member 25 may be constructed of any suitable material, whether porous or not, and coated or covered with a thromboresistant material or membrane that is impermeable to blood so that blood cannot pass through the flow control member. For example, the flow control member 25 may have a generally cage-like or relatively open cell construction and be covered with a suitable thromboresistent membrane, such as a membrane constructed of Nitinol whereby blood cannot pass through it. It is understood, however, that any suitable material may be used to construct the flow control member 25 as long as the flow control member is not permeable to blood flowing within the blood vessel lumen L.

The flow control member 25 is retained within the blood vessel V, such as by being attached to the retention member 23 as in the illustrated embodiment, or directly to the blood vessel (in which instance the retention member may be omitted). In one suitable embodiment the flow control member 25 may be attached to the retention member 23 for conjoint delivery to and deployment in the blood vessel V along with the retention member. It is contemplated, however, that the retention member 23 may instead be delivered to and deployed in the blood vessel V in advance of the flow control member 25, with the flow control member being inserted in and attached to the retention member upon subsequent delivery of the flow control member to a predetermined location within the retention member. It is also contemplated that the flow control member 25 may be constructed for releasable attachment to the retention member 23 to permit adjustment (e.g., movement) of the flow control member relative to the retention member.

The flow control member 23 is suitably sized and shaped to alter the path of blood flow through the blood vessel, at least in the regions just upstream from and at the aneurysm as illustrated by the flow direction arrow F2 in FIG. 1. More suitably, the flow control member 23 projects or extends radially inward of the blood vessel luminal surface S (e.g., in the illustrated embodiment, from the retention member inner surface 29 in the illustrated embodiment) a distance sufficient to alter the blood flow enough so that blood flowing downstream of the flow control member does not flow into the aneurysm A with the same hemodynamic force at which it otherwise would absent the flow control member.

As one example, the flow control member 25 may be sized to extend radially inward of the blood vessel luminal surface S a greatest distance d in the range of about 5 percent to about 60 percent of the diameter D of the blood vessel V at the predetermined location at which the flow control member is to be deployed, more suitably in the range of about 10 percent to about 50 percent, and even more suitably in the range of about 10 percent to about 30 percent of the diameter D of the blood vessel V at the predetermined location of deployment. As used herein, the term "greatest distance" in reference to the distance d that the flow control member 25 extends inward from the blood vessel wall W refers to the point at which the flow control member extends furthest inward from the vessel wall luminal surface S, recognizing that the inward extension of the flow control member need not be uniform, and not to any particular limit on such a distance.

As seen best in FIG. 1, for example, the flow control member 25 is shaped in longitudinal profile generally in the manner of a ramp or ski-bump with a relatively gradual or at least ramped increase in distance of a luminal surface 31 (e.g., the surface facing and exposed to the blood flow through the lumen L of the blood vessel V) of the flow control member radially inward away from the blood vessel inner surface. The length of the flow control member is in the range of about 50 percent to about 300 percent of the diameter D of the blood vessel V, and more suitably in the range of about 100 percent to about 200 percent.

The illustrated flow control member 25 is also generally ovate in cross-section (FIG. 2) so that a wall-facing surface 33 of the flow control member generally follows the circumferential contour of the luminal surface S of the blood vessel wall W. It is understood, however, that the flow control member 25 may extend transversely within the lumen L out of engagement with a circumferential extent of the luminal surface S and remain with the scope of this invention. The transverse width (or circumferential extent) of the flow control member 25 is suitably at least equal to and more suitably greater than the transverse width (or circumferential extent) of the aneurysm neck N. As one example, it is contemplated that the transverse width of the flow control member 25 may correspond to a circumferential (e.g., arcuate) segment of the blood vessel luminal surface S (and hence of the tubular retention member 23 in the illustrated embodiment) in the range of about 20 degrees to about 180 degrees, and more suitably in the range of about 90 degrees to about 120 degrees.

It is understood that the size and geometry of the flow control member 25 may be other than as set forth above and is generally dependent on at least the geometry of the aneurysm A, the parent blood vessel V and adjacent downstream branches thereof. In one suitable embodiment, a greatest transverse cross-sectional area of the flow control member 25 determines the relative constriction of blood flow through the lumen L of the blood vessel V. The term "greatest transverse cross-sectional area" in reference to the flow control member 25 refers to the transverse cross-section of the flow control member at which the cross-sectional area is greater than at any other location along the length of the flow control member and does not imply any particular maximum or other limitation on the size and shape of the flow control member.

In one particularly suitable embodiment, the greatest transverse cross-sectional area of the flow control member 25 is about 50 percent or less of the blood vessel cross-sectional area at the location of the greatest transverse cross-sectional area of the flow control member, more suitably about 35 percent or less, and even more suitably about 25 percent or less to reduce the risk of overly constricting blood flow past the flow control member.

Figure 3:
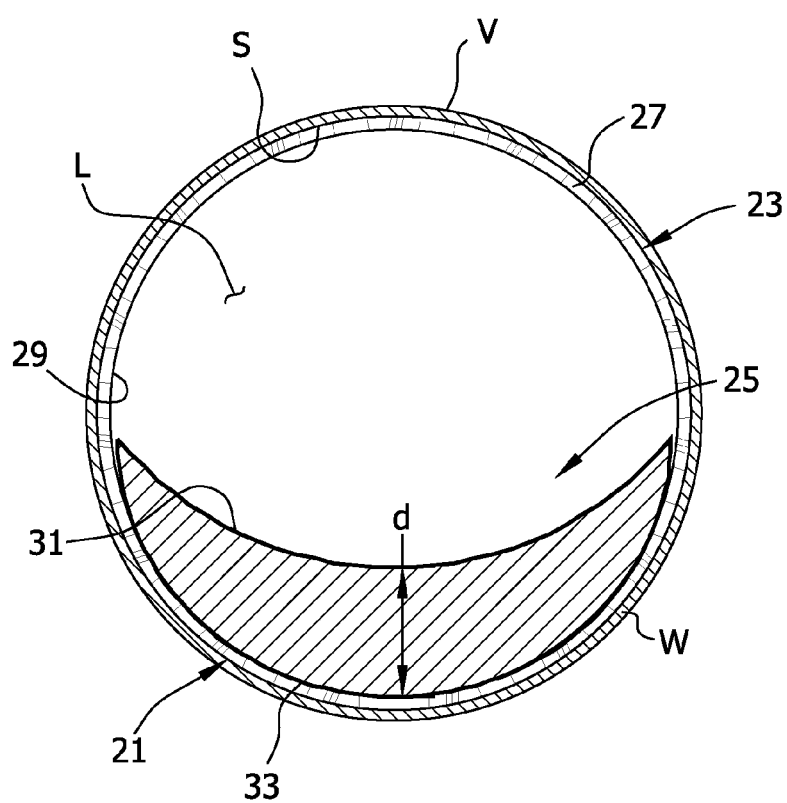
FIG. 3 is a cross-section similar to FIG. 2 but of another embodiment of an apparatus for treating an aneurysm.
Figure 4:
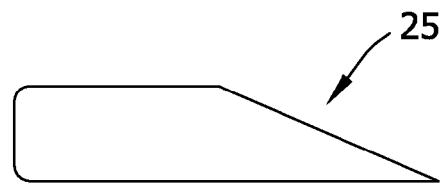
FIG. 4 is a schematic illustration of an alternative flow control member.
Figure 5:
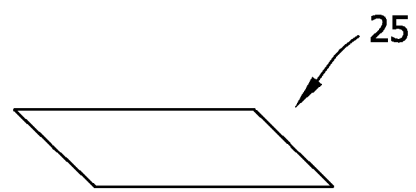
FIG. 5 is a schematic illustration of another alternative flow control member.
Figure 6:
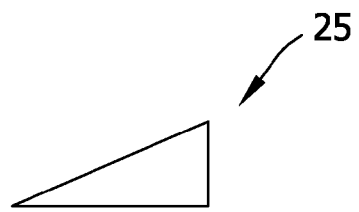
FIG. 6 is a schematic illustration of yet other alternative flow control members.
Figure 7:
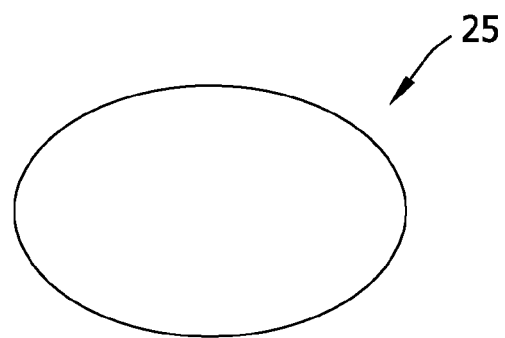
FIG. 7 is a schematic illustration of still another alternative flow control member.
Figure 8:
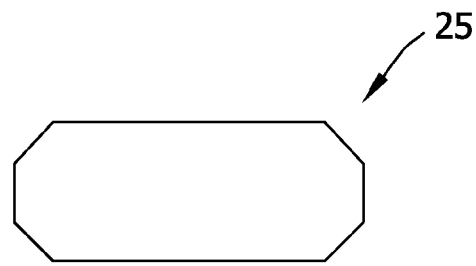
FIG. 8 is a schematic illustration of another alternative flow control member.

FIG. 3 illustrates another embodiment of an aneurysm treatment apparatus 21 similar to that of FIG. 1 with a flow control member 25 being generally moon-shaped, or having a concave luminal surface in cross-section and lining a substantially greater circumferential segment of the blood vessel luminal surface S (and hence the retention member 23) than the flow control member of FIG. 1. FIGS. 4-8 illustrate, without limitation, additional suitable flow control member sizes and geometries.

The flow control member 25 is suitably deployed in the blood vessel V (and, in the illustrated embodiment, retained by the retention member 23) at a predetermined location that is at least in part and is more suitably entirely upstream of the aneurysm neck N so the neck remains substantially unoccluded by the apparatus 21. In particular, the location at which the flow control member 25 extends radially inward its greatest distance from the blood vessel luminal surface S is disposed longitudinally upstream from the neck N of the aneurysm A. This longitudinal location of the flow control member 25 upstream from the aneurysm A is generally dependent at least in part on the length of the flow control member, the size of the flow control member and the size of the aneurysm neck N.

Figure 9A:
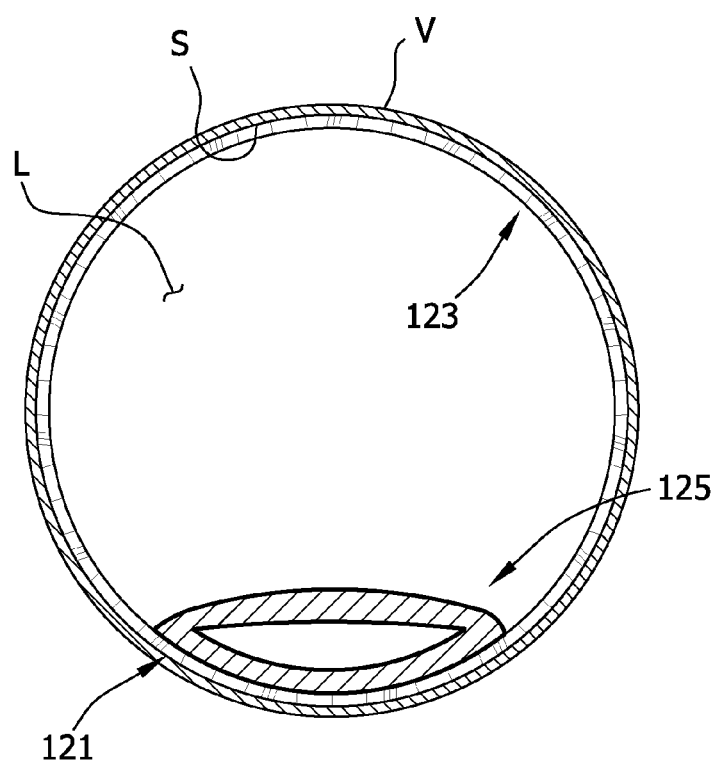
FIG. 9A is a cross-section similar to FIG. 2 but of another embodiment of apparatus for treating an aneurysm in which the flow control member of the apparatus is expandable, the flow control member being illustrated in its generally unexpanded configuration.
Figure 9B:
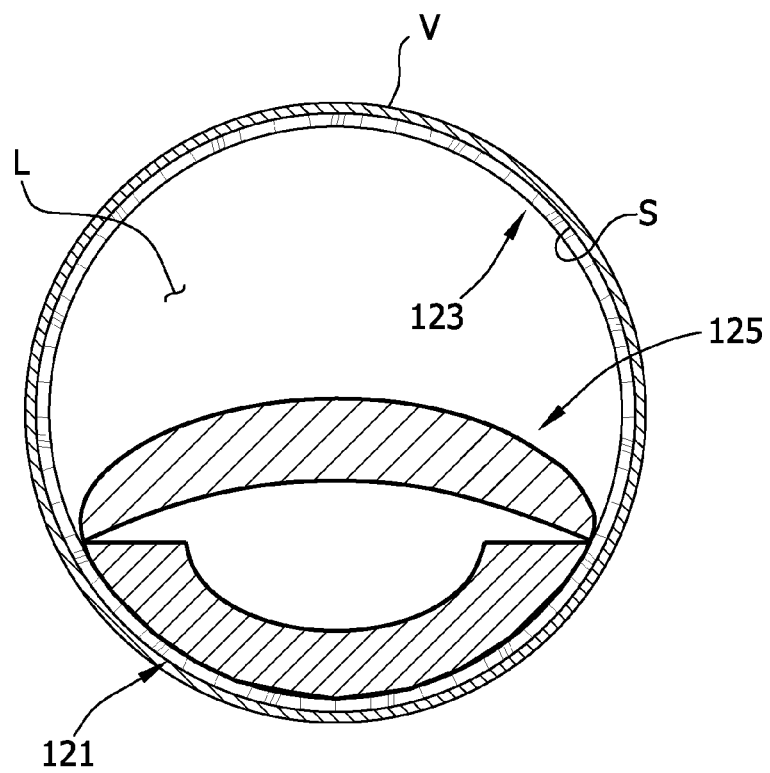
FIG. 9B is a cross-section similar to FIG. 9A with the flow control member being illustrated in its expanded configuration.

FIG. 9A is illustrative of another embodiment of apparatus 121 for treating an aneurysm A in which a flow control member 125 is similar to that of the embodiment of FIG. 1 with the exception that the flow control member of this embodiment is expandable. In particular, this flow control member 125 is configurable from a relatively compact configuration (FIG. 9A) for ease of delivering and deploying the flow control member into the blood vessel V as illustrated in FIG. 9A, and an expanded configuration (FIG. 9B) in which the flow control member is expanded to its desired size. In one exemplary embodiment, the flow control member 25 may comprise an elastic material, a shaped memory alloy (SMA) or other suitable material that is compressible into a compact configuration for delivery into the blood vessel V (e.g., along with the retention member) and then allowed to expand (e.g., elastically recover) upon deployment within the blood vessel at the predetermined location. The flow control member 125 may be constructed in whole of an elastic material, such as a thromboresistant elastic polymer, or of an outer shell constructed of a blood impermeable material such as Nitinol and an inner core of the elastic polymer. In another embodiment the expandable flow control member 125 may be inflatable, whereby the flow control member is at least partially deflated to define the compact configuration for delivery into the blood vessel V. The inflatable flow control member 125 is then inflated to the desired size thereof upon deployment within the blood vessel.

While in the illustrated embodiments of FIGS. 1-9B the flow control member 25, 125 is generally a single-piece flow control member, it is contemplated that the flow control member may comprise multiple pieces. In some embodiments these multiple pieces may be stackable, or arrangeable side-by-side or otherwise to permit adjustment of the flow control member 25, 125 size and shape (e.g., by adding or removing pieces thereof). It is also understood that more than one flow control member 25, 125 may be deployed in the lumen L of the blood vessel V upstream of the aneurysm A to alter the blood flow within the blood vessel.

To deploy and use the treatment apparatus 21 according to one embodiment of a method for treating an aneurysm, an endovascular device, such as a microcatheter (not shown) is used to deliver the retention member 23 and flow control member 25 conjointly (e.g., when the flow control member is pre-attached to the retention member) to a location in the blood vessel V to be treated, with the retention member at least in part upstream from the aneurysm A. In a particularly suitable embodiment at least the retention member 23 is in a relatively compact (e.g., folded, collapsed, compressed, etc.) configuration to facilitate delivery of the retention member to the target blood vessel V location. Where the flow control member 25 is configured to be expandable, the flow control member is also suitably compacted along with the retention member 23.

Once the target location is reached, the retention member 23 (and flow control member 25) is released by the microcatheter within the blood vessel V. The retention member 23 expands slightly to engage the luminal surface S of the blood vessel wall W to thereby retain or generally anchor the retention member at the target location in the blood vessel V. Because the retention member 23 is relatively thin and lies against the luminal surface S of the blood vessel wall W, it has little or no effect on the flow path of blood through the blood vessel V. With the retention member 23 at its target location, the flow control member 25, having been deployed conjointly with the retention member is also at its target location upstream from the aneurysm A to be treated. Where necessary, the retention member 23 (and hence the flow control member 25) may be rotated using the microcatheter (e.g., before the retention member is released therefrom) so that the flow control member is substantially longitudinally aligned with the portion of the blood vessel luminal surface S at which the neck N of the aneurysm A opens. That is, so that the wall-facing surface 33 of the flow control member 25 covers a circumferential segment of the blood vessel wall W that corresponds to the circumferential segment of the blood vessel wall that opens to the neck N of the aneurysm A.

In other embodiments, where the flow control member 25 is initially separate from the retention member 23, the retention member is deployed using a microcatheter in the manner described above, and a guide wire (not shown) or other suitable delivery device is used to deliver and deploy the flow control member into attachment with the retention member at the target location of the flow control member.

In either of the above embodiments, once the flow control member 25 is deployed it is allowed to expand (if it is elastically expandable), or it is inflated (if it is inflatable) using a suitable air delivery tube. The flow control member 25 now extends radially inward of the luminal surface S of the blood vessel wall W upstream from the aneurysm while the aneurysm itself (e.g., the neck N thereof) remains substantially unoccluded by the treatment apparatus 21 or other packing elements. Blood flowing in the direction F1 within the blood vessel V encounters the flow control member 25 and, because the flow control member is impermeable to blood flowing with the blood vessel, the flow path of the blood is altered in the area of the flow control member to flow over the flow control member as indicated by the flow arrow F2 in FIG. 1. As the blood flows downstream of the flow control member 25, much of the faster moving blood is now further away from the open neck N of the aneurysm A (e.g., instead of flowing adjacent the luminal surface S and into the aneurysm) as indicated by the flow arrow F2 until the blood flows further downstream beyond the aneurysm A.

As a result, the hemodynamic forces at the aneurysm A are substantially reduced or even eliminated, thereby isolating the aneurysm without having to place devices directly into or completely covering the aneurysm.

Figure 10:
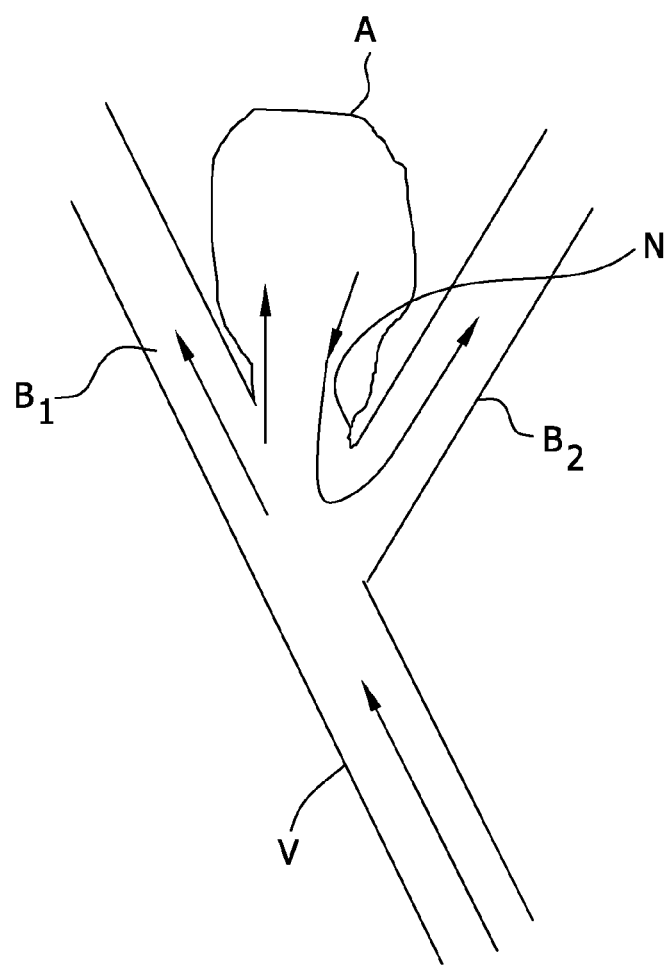
FIG. 10 is a schematic illustration of a bifurcation-type blood vessel configuration and an aneurysm located at the bifurcation point.

FIG. 10 schematically illustrates a bifurcation-type blood vessel arrangement in which an aneurysm A is located at the bifurcation point where the parent blood vessel V bifurcates into a pair of branch blood vessels B1, B2. In particular, a neck N of the aneurysm A is open to both branch blood vessels B1, B2 at the point of bifurcation. As illustrated by the flow arrows in FIG. 10, in such an aneurism A some of the blood flowing through the parent blood vessel V flows into the aneurism generally adjacent one of the branches B1, circulates within the aneurysm and the exits through the neck N adjacent the other one of the branches B2 for flow through this other one of the branches. In the illustrated embodiment, the branch blood vessels B1, B2 are each of a diameter that is less than that of the parent blood vessel.

Figure 11:
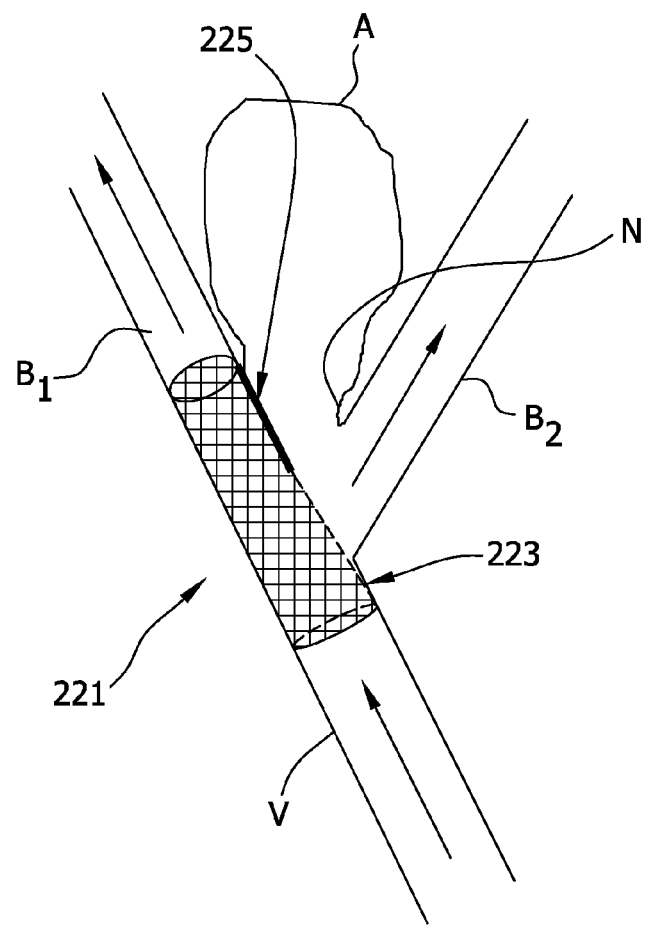
FIG. 11 is a schematic illustration of a bifurcation-type blood vessel configuration and aneurysm similar to FIG. 10 with another embodiment of apparatus for treating an aneurysm in such a blood vessel configuration.
Figure 11A:
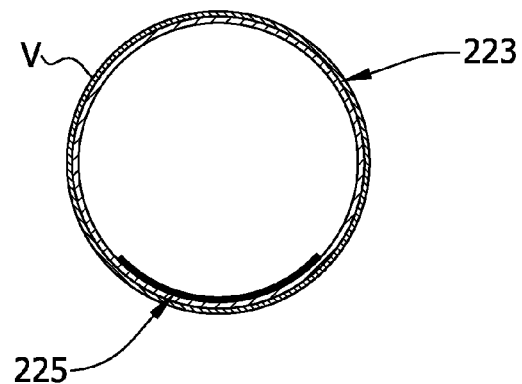
FIG. 11A is a transverse cross-section taken through a flow control member of the apparatus of FIG. 11.

In another embodiment of an apparatus 221 and method for treating an aneurism A, illustrated in FIGS. 11 and 11A, a retention member 223 is constructed to be similar to that of FIGS. 1 and 2 and is deployed generally at the bifurcation point between the parent blood vessel V and the branch blood vessels B1, B2. More suitably, in this embodiment the retention member 223 is constructed for positioning in part (e.g., along a longitudinal segment thereof) within the parent blood vessel V where the parent blood vessel opens into the branch blood vessels B1, B2, and in part (e.g., along a separate longitudinal segment) within the branch blood vessel B1 adjacent to the portion of the aneurism neck N through which blood would otherwise enter the aneurism A absent the apparatus 221 set forth herein. Accordingly, as illustrated in FIG. 11, the diameter of the retention member 223 generally decreases in a tapered manner from the segment disposed within the parent blood vessel V to the segment disposed with the smaller diameter branch blood vessel B1, in accordance with the decreasing diameter of the blood vessels.

The retention member 223 is suitably constructed to be generally cage-like or open celled (FIG. 11), or otherwise at least permeable to the flow of blood to permit blood flow through a side wall 235 of the retention member into the other branch blood vessel B2. A flow control member 225 (FIGS. 11 and 11A) is attached to the retention member 223 generally within the one branch blood vessel B1 and extends upstream past the neck N of the aneurysm A. However, the flow control member 225 does not extend upstream to the parent blood vessel V where the parent flood vessel opens to the other branch blood vessel B2.

In the illustrated embodiment the flow control member 225 is in the form of a blood impermeable liner that lines a portion of the retention member 223 to prevent blood from flowing through the side wall of the retention member at the location of the flow control member. It is understood, however, that the flow control member 225 may be shaped in accordance with any of the sizes and/or geometries of FIGS. 1-9B, or other suitable shape without departing from the scope of this invention. The flow control member 225 may also be constructed of any of the materials described previously as being suitable for construction of the flow control member of FIGS. 1-9B. The flow control member 225 is also suitably sized in transverse width (FIG. 11A) to cover a circumferential extent of the retention member corresponding to the circumferential extent of the portion of the neck N of the aneurysm A adjacent the blood vessel branch B1.

As can be seen from FIG. 11, the neck N of the aneurysm A is not fully occluded or blocked off by the flow control member 225. Rather, in accordance with another method for treating aneurysms, blood flowing downstream through the parent blood vessel V toward the aneurism A enters the upstream end of the retention member 223. Some of the blood flows into the other branch blood vessel B2 upstream of the flow control member 225 so that the blood flow is sufficiently remote from the aneurysm neck N to reduce or eliminate the hemodynamic forces of flow into the aneurysm A. Additional blood, flowing toward the downstream end of the retention member 225, contacts the flow control member 225 so that the blood flow path blood is altered (e.g., prevented from flowing into the aneurysm A) and is more particularly deflected into the one branch blood vessel B1 for subsequent flow therethrough.

Figure 12:
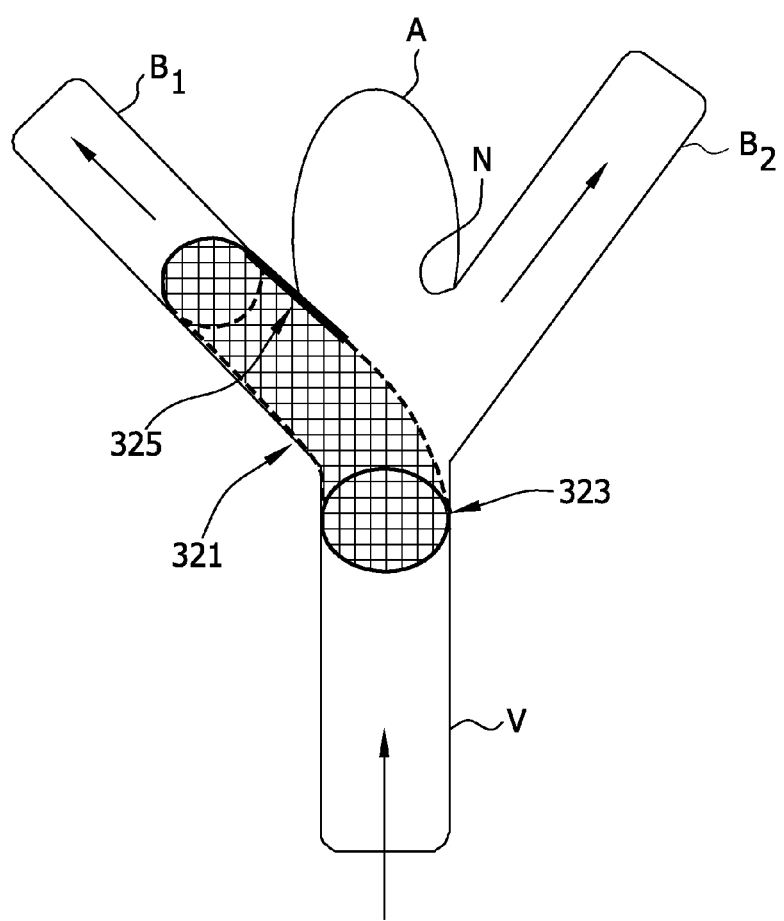
FIG. 12 is a schematic illustration of another bifurcation-type blood vessel arrangement and an aneurysm located at the bifurcation point, and another embodiment of apparatus for treating an aneurysm in such an blood vessel configuration.

FIG. 12 illustrates another embodiment of apparatus 321 for treating an aneurysm A, particularly in a bifurcation-type blood vessel arrangement. The apparatus 321 is substantially similar to that of FIG. 11 but with the retention member 323 being sufficiently flexible to permit bending of the retention member as it extends from the parent blood vessel V through the bifurcation joint and into the one branch blood vessel B1. Construction of the retention member 325 and operation of the apparatus 321 is otherwise substantially the same as for the embodiment of FIG. 11.

Figure 13:
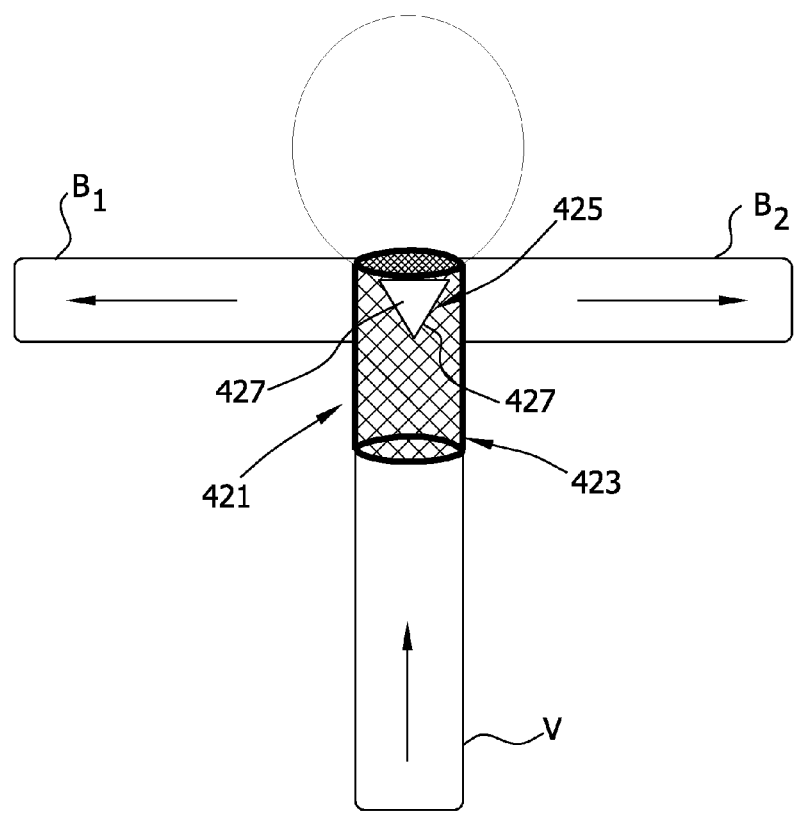
FIG. 13 is a schematic illustration of a terminal-type blood vessel configuration with an aneurysm located at the terminus of the parent artery, and another embodiment of apparatus for treating an aneurysm in such a blood vessel configuration.
Figure 14A:
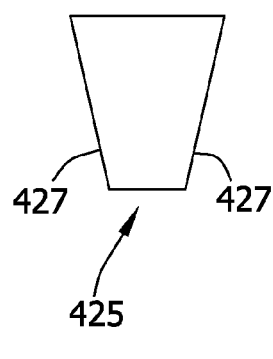
FIGS. 14A-D are schematic illustrations of various flow control members useful with the aneurysm treatment apparatus of FIG. 13.
Figure 14B:
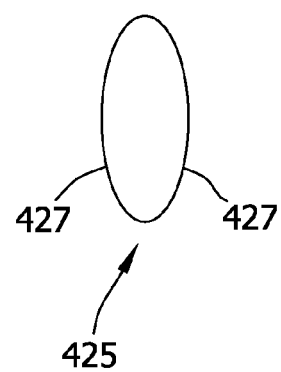
Figure 14C:
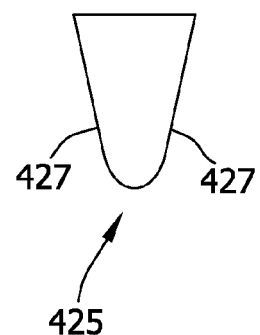
Figure 14D:
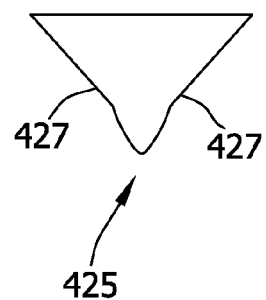

In a terminal-type blood vessel configuration, illustrated in FIG. 13, the parent blood vessel V terminates and divides into two separate branch flows through respective branch blood vessels B1, B2. In FIG. 13, an aneurism A has grown at the terminal junction of the parent blood vessel V with the branch vessels B1, B2. Another embodiment of an apparatus and method for treating such an aneurism A is generally indicated at 421 and comprises a retention member 423 and a flow control member 425. The retention member 423 of this illustrated embodiment is substantially the same as that of FIGS. 1 and 2 and has an upstream end positionable within the parent blood vessel V and a downstream end or terminus that abuts or otherwise terminates adjacent the neck N of the aneurysm A. In the illustrated embodiment, the downstream end of the retention member 423 is suitably closed or capped, such as by a liquid permeable closure constructed of the same material as the retention member. The closure may have a porosity that is generally equal to or more suitably less than that of the retention member sidewall. It is understood, however, that the downstream end of the retention member 423 may be open, or it may be capped by a liquid impermeable structure, without departing from the scope of this invention.

A flow control member 425 is deployed within the retention member 423, such as by being attached thereto either prior to placement of the retention member into the blood vessel V or subsequent thereto. The flow control member 425 of this embodiment is suitably configured for diverting blood flowing from the parent blood vessel V into each of the respective branch blood vessels B1, B2 while inhibiting blood against flowing into the aneurysm A. For example, in the illustrated embodiment the flow control member 425 is generally conical in shape and defines at least one deflection surface 427 of the flow control member. The deflection surface 427 is angled relative to the direction of blood flow coming from the parent blood vessel V.

It is contemplated that the flow control member 425 may be of a shape other than that illustrated in FIG. 13, such as, without limitation, any of the flow control member shapes illustrated in FIGS. 14A, 14B, 14C and 14 or other suitable shapes as long as the flow control member is configured to define a deflection surface 427 that is angled relative to the direction of blood flow coming from the parent blood vessel V. It also understood that while the flow control member 425 illustrated in FIG. 13 is located and oriented generally concentrically with the patent blood vessel V, in other embodiments the flow control member may be transversely offset from a concentric position, or angled slightly relative thereto, without departing from the scope of this invention.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

We claim:

1. Apparatus for treating an aneurysm, the apparatus comprising:
   a retention member positionable within a blood vessel at least in part upstream from an aneurysm and having an outer surface engageable with a blood vessel wall; and
   a flow control member retained by the retention member and adapted to extend radially inward of the blood vessel wall upstream from the aneurysm to increase the flow rate of blood prior to the blood flowing past the aneurysm and to direct the blood flowing past the aneurysm away from the aneurysm.

2. The apparatus set forth in claim 1 wherein the flow control member is impermeable to blood flow therethrough.

3. The apparatus set forth in claim 1 wherein the blood vessel in which the apparatus is located has an inner diameter D, the flow control member being sized to extend radially inward of the blood vessel wall a distance d in the range of about 5 percent to about 60 percent of the inner diameter D of the blood vessel.

4. The apparatus set forth in claim 3 wherein the flow control member is sized to extend radially inward of the blood vessel wall a distance d in the range of about 10 percent to about 30 percent of the inner diameter D of the blood vessel.

5. The apparatus set forth in claim 1 wherein the flow control member is configurable between a compact configuration to facilitate delivery of the flow control member into the blood vessel and an expanded configuration upon positioning of the flow control member at a predetermined location within the blood vessel.

6. The apparatus set forth in claim 5 wherein the flow control member is elastically expandable from its compact configuration to its expanded configuration.

7. The apparatus set forth in claim 1 wherein the flow control member is attached to the retention member to permit conjoint delivery of the retention member and flow control member into the blood vessel as a single unit.

8. The apparatus set forth in claim 1 wherein the flow control member is a first flow control member, the apparatus further comprising a second flow control member retained by the retention member and extending radially inward of the blood vessel wall upstream from the aneurysm.

9. The apparatus set forth in claim 1 wherein the retention member is generally tubular and has a side wall and an internal cross-sectional dimension, the flow control member being retained by the side wall of the retention member and extending transversely inward thereof a distance d in the range of about 5 percent to about 60 percent of the internal cross-sectional dimension of the retention member.

10. The apparatus set forth in claim 9 wherein the side wall of the retention member defines an internal circumference of the retention member, the flow control member extending circumferentially about the internal circumference substantially less than the entire internal circumference of the retention member.

11. Apparatus for treating an aneurysm, the apparatus comprising:
a retention member positionable within a blood vessel at least in part upstream from an aneurysm and having an outer surface engageable with a blood vessel wall, the retention member being generally tubular and having a side wall, the side wall of the retention member defining an internal circumference of the retention member; and
a flow control member retained by the retention member and adapted to extend radially inward of the blood vessel wall upstream from the aneurysm to alter the blood flow within the blood vessel prior to the blood flowing past the aneurysm, the flow control member extending circumferentially about the internal circumference substantially less than the entire internal circumference of the retention member.

\* \* \* \* \*